(12) United States Patent
Skalli

(10) Patent No.: US 10,478,141 B2
(45) Date of Patent: Nov. 19, 2019

(54) METHOD FOR ESTIMATING THE DISTRIBUTION OF BONE MINERAL DENSITY IN AT LEAST ONE PORTION OF A PERSON'S SKELETON

(71) Applicants: AMVALOR, Paris (FR); ECOLE NATIONALE SUPERIEURE D'ARTS ET METIERS, Paris (FR)

(72) Inventor: Wafa Skalli, Paris (FR)

(73) Assignees: AMVALOR, Paris (FR); ECOLE NATIONALE SUPERIEURE D'ARTS ET METIERS, Paris (FR)

( * ) Notice: Subject to any disclaimer, the term of this patent is extended or adjusted under 35 U.S.C. 154(b) by 184 days.

(21) Appl. No.: 15/572,374

(22) PCT Filed: May 4, 2016

(86) PCT No.: PCT/EP2016/060035
§ 371 (c)(1),
(2) Date: Nov. 7, 2017

(87) PCT Pub. No.: WO2016/177798
PCT Pub. Date: Nov. 10, 2016

(65) Prior Publication Data
US 2018/0146942 A1    May 31, 2018

(30) Foreign Application Priority Data

May 7, 2015    (FR) ...................... 15 54150

(51) Int. Cl.
*A61B 6/02*      (2006.01)
*A61B 6/00*      (2006.01)

(52) U.S. Cl.
CPC ............... *A61B 6/505* (2013.01); *A61B 6/02* (2013.01); *A61B 6/4007* (2013.01);
(Continued)

(58) Field of Classification Search
CPC ......... A61B 6/505; A61B 6/5217; A61B 6/02; A61B 6/4007; A61B 6/4014; A61B 6/5205
See application file for complete search history.

(56) References Cited

U.S. PATENT DOCUMENTS 5,850,836 A * 12/1998 Steiger ................. A61B 6/4441
                                                            600/300
5,917,877 A *  6/1999 Chiabrera .............. A61B 6/482
                                                             378/207
(Continued)

FOREIGN PATENT DOCUMENTS

FR           2 856 170      12/2004
WO      WO 2008/146069     12/2008

*Primary Examiner* — David P Porta
*Assistant Examiner* — Fani Boosalis
(74) *Attorney, Agent, or Firm* — Muncy, Geissler, Olds & Lowe, P.C.

(57) ABSTRACT

A method of estimating the distribution of bone mineral density in at least one portion of a person's skeleton. The method includes generating a geometrical representation of the portion of the skeleton; a geometrical representation in three dimensions of at least one portion of the outline of the person; and first and second X-ray images; and using software to estimate: a value for the thickness of soft tissue through which the given X-ray has passed; an attenuation coefficient of the soft tissues that have been passed through; a value for the thickness of bone tissue through which the given X-ray has passed; and using the thickness value for the soft tissue through which the given X-ray has passed, and a value for the attenuation of the given X-ray due to the thickness of the bone tissue through which it has passed, the software estimates a value representative of the bone mineral density of the bone tissues through which the given X-ray has passed.

13 Claims, 1 Drawing Sheet

(52) U.S. Cl.
CPC .......... *A61B 6/4014* (2013.01); *A61B 6/4266* (2013.01); *A61B 6/5205* (2013.01); *A61B 6/5217* (2013.01)

(56) References Cited

U.S. PATENT DOCUMENTS

| | | |
|---|---|---|
| 2001/0004394 A1 | 6/2001 | Siffert et al. |
| 2002/0075997 A1 | 6/2002 | Unger et al. |
| 2006/0204069 A1 | 9/2006 | Le Bras et al. |
| 2011/0058725 A1 | 3/2011 | Markwardt et al. |

* cited by examiner

METHOD FOR ESTIMATING THE DISTRIBUTION OF BONE MINERAL DENSITY IN AT LEAST ONE PORTION OF A PERSON'S SKELETON

The invention relates to the field of methods of estimating the distribution of bone mineral density in at least a portion of a person's skeleton.

BACKGROUND OF THE INVENTION

Methods are known for characterizing the distribution of bone mineral density in people's skeletons. Such characterization can be particularly useful for diagnosing a person's osteoporosis risk.

For this purpose, X-ray images are used of the person's skeleton, which X-rays are taken by projecting X-rays at different energy levels from an X-ray source, such as an X-ray tube, onto the person and then detecting, for each of the energy levels, the extent to which the X-rays are attenuated by that person's tissues.

Analyzing the differential attenuation between tissues makes it possible to visualize the distribution per unit area, or "areal" distribution, of bone mineral density in a plane onto which the person's skeleton is projected.

A drawback of that method, which is known under the name of "Dual X-ray absorptiometry", is that when the X-ray apparatus requires time between generating two energy levels, during which time the person must remain completely still, since otherwise differential analysis cannot be undertaken between the two images obtained at two energy levels.

Another problem of that method is that it requires X-ray operators to have a high level of training, and it also requires specific installations for generating X-rays at different energy levels.

OBJECT OF THE INVENTION

An object of the present invention is to provide an alternative method for estimating the distribution of bone mineral density in at least a portion of a person's skeleton.

SUMMARY OF THE INVENTION

In order to satisfy this object, the invention proposes an estimation method for estimating the distribution of bone mineral density in at least one portion of a person's skeleton, the skeleton being made up of bone tissue, the bone tissue being surrounded by soft tissue, itself surrounded by an outline of the person.

The method is essentially characterized in that it comprises generating:
a geometrical representation in three dimensions of said portion of the person's skeleton;
a geometrical representation in three dimensions of at least one portion of the outline containing said portion of the person's skeleton;
at least one first X-ray image of said at least one portion of the skeleton, this first image being generated by observing a projection onto a first detection surface of X-rays, coming from a first source, the first image being generated by projecting X-rays and representing the person as observed from a first observation angle of incidence; and
at least one second X-ray image of said at least one portion of the skeleton, the second image being generated by projecting X-rays and representing the person as observed from a second observation angle of incidence distinct from the first observation angle of incidence; and then
using predetermined software and for a plurality of given X-rays selected from among said projected X-rays, estimating for each given X-ray:
a value for the thickness of soft tissue through which the given X-ray has passed;
a value for the thickness of bone tissue through which the given X-ray has passed; and
a value for the overall attenuation of the given X-ray between its source and its projection onto the detection surface onto which it is projected; and
using the thickness value for soft tissue through which the given X-ray passes, and using an estimate for an attenuation coefficient of the soft tissues through which the given X-ray passes, deducing firstly a value for the attenuation of the given X-ray due to the thickness of soft tissue through which it has passed and secondly a value for the attenuation of the given X-ray due to the thickness of bone tissue through which it has passed; and then
using the value for the thickness of bone tissue through which the given X-ray has passed, the value for the attenuation of the given X-ray due to the thickness of bone tissue through which it has passed, and the overall value for attenuation of the given X-ray, the software estimates a value representative of the bone mineral density of the bone tissue through which the given X-ray has passed.

For understanding the invention, the term "X-ray" corresponds to at least one X-ray or to a plurality of mutually parallel X-rays forming a beam.

Still for understanding the invention, the term "attenuation coefficient" designates a coefficient suitable for quantifying the attenuation of the intensity of a given X-ray due to a given material as a function of the thickness of that material through which the X-ray passes.

Each X-ray projected from a projection source propagates through three-dimensional space to the detection surface corresponding thereto by following a straight line path. Thus, each projected ray passes through the soft tissues and the bone tissues of the person's skeleton by following a straight line. Knowing the source of the ray and its projection point, i.e. its point of impact on the detection surface, it is possible to determine the position in three-dimensional space of each X-ray relative to the detection surfaces and relative to the sources, knowing that these detection surfaces and sources are fixed relative to one another, at least during the time needed for projection, and that the relative positions of the detection surfaces and of the sources are known, in particular by calibrating the radiological environment.

Knowing that each X-ray passing through a material is attenuated by that material as a function of an attenuation coefficient that is specific to that material, it is found that each X-ray passing through the outline of the person, through the soft tissues, and/or through the bone tissues of that person, is attenuated by the set of tissues through which it has passed.

Since each point of the X-ray image presents a gray scale or color or contrast level that is representative of or a function of the intensity of the X-ray reaching a corresponding point of the detection surface, it is possible, by observing each point of the X-ray image, to determine an intensity level for the X-ray(s) that has/have been projected onto the corresponding point of the corresponding detection surface.

Knowing the intensity of each X-ray emitted by the given source that corresponds thereto, and knowing its intensity level on reaching the corresponding detection surface, it is possible from each point of an X-ray image to determine a level for the attenuation suffered by the X-ray(s) that have reached and/or been projected onto that point from the corresponding source.

Thus, from the contrast between the points of the image, there can be obtained the projected limits of the various soft tissues, of the various bone tissues, and of the person's outline.

Since the X-ray sources and the detection surfaces are fixed in three dimensions and located in three dimensions using a three-dimensional reference frame, and since the person retains the same posture throughout the projection time, it is possible by observing the first and second X-ray images to deduce (to within quantifiable uncertainties) the exact positions in said three-dimensional reference frame of each point of the person that has been passed through:
- firstly by an X-ray or an X-ray beam coming from the first source and projected onto the first detection surface, as shown in the first X-ray image; and
- secondly by another X-ray or X-ray beam used to generate the second X-ray image.

It should be observed that the change in the observation angle of incidence between the first and second X-ray images may be obtained:
- either by moving the X-ray source relative to the observed person, while ensuring that the person retains the same posture between the takes necessary for obtaining the first and second images;
- or else by using two distinct X-ray sources and/or two distinct detection surfaces.

Thus, the analysis of the first and second X-ray images taken with observations of the person at distinct angles of incidence, i.e. angles that are different from each other, makes it possible:
- firstly to have a three-dimensional representation of that person's outline and soft and bone tissues; and
- secondly to have an estimate of the overall attenuation suffered by an X-ray passing through a plurality of soft tissues and possibly a plurality of bone tissues of that person.

Nevertheless, merely estimating an overall attenuation value for the given X-ray between its source and its projection onto the detection surface is not sufficient to be able to estimate the bone density of the bone tissues through which the given X-ray has passed. Specifically, a fraction of this overall attenuation value for the given X-ray is associated not with bone tissues but with soft tissues.

The method of the invention provides a solution to this problem in that it makes it possible to estimate the fraction of the attenuation of a given X-ray that is associated solely with the soft tissues through which the given X-ray has passed, and the fraction of the attenuation of the given X-ray that is associated with the bone tissues through which the X-ray has passed.

Specifically, the method of the invention makes use of:
- a geometrical representation in three dimensions of said portion of the person's skeleton; and
- a geometrical representation in three dimensions of at least a portion of the outline containing said portion of the person's skeleton; and
- knowing the position of each given X-ray relative to these geometrical representations of the portion of the skeleton and of the outline, it is possible by means of software to calculate:
- firstly the total distance traveled by the given X-ray through soft tissues situated within the outline of the person; and
- secondly the total distance traveled by the same given X-ray through bone tissues situated within the outline of the person.

These two distances correspond respectively to:
- a value for the thickness of soft tissue through which the given X-ray has passed; and
- a value for the thickness of bone tissue through which the given X-ray has passed.

Various means exist for estimating the attenuation coefficient of the person's soft tissues.

By way of example, it is possible to look for a particular X-ray that passes only through the person's soft tissues without passing through bone tissue.

In order to estimate the attenuation coefficients of the soft tissues of the person, the software looks for a particular X-ray that passes solely through soft tissues of the person without passing through bone tissues, and from the position of this particular X-ray and from the geometrical representation in three dimensions of the portion of the outline, the software estimates the value of the thickness of soft tissues through which this particular X-ray passes, and by observing a projection point of this particular X-ray, the software determines a value for the attenuation to which the particular X-ray is subjected on passing solely through soft tissues of the person, and then knowing said thickness value for the soft tissues through which a particular X-ray passes and said value for the attenuation to which the particular X-ray is subjected, the software calculates the attenuation coefficient associated solely with the person's soft tissues.

This is an attenuation coefficient that is specific to the soft tissues of the person.

In order to improve accuracy, it is naturally entirely possible to calculate this coefficient for various X-rays that pass through soft tissues only, in a region that is assumed to be uniform, and to estimate the attenuation coefficient as an average of the various values that are obtained.

Thereafter, for any given X-ray, knowing:
- the attenuation coefficient of the person's soft tissues; and
- the thickness of soft tissue through which the given X-ray passes, the software calculates:
- firstly a value for the attenuation of the given X-ray due to the thickness of soft tissue through which it has passed; and
- secondly, using the intensity $I_0$ of this given ray at its source and the intensity $I$ of this given ray as detected on the detection surface onto which it is projected, the software calculates an overall attenuation value for this given X-ray between the source and the detection surface onto which it is projected; and then
- by correcting the overall attenuation value of the given X-ray so as to take account of said value for the attenuation of the given X-ray due to the thickness of soft tissue through which it has passed, the software calculates the value for the attenuation of the given X-ray due to the thickness of bone tissue through which it has passed.

Thus, for each given X-ray, it is possible to calculate the value for the attenuation of the given X-ray due solely to the thickness of the bone tissue through which it has passed.

It may be decided that said value representative of the bone mineral density of bone tissue through which the given X-ray passes is an attenuation coefficient of the bone tissue through which the given X-ray passes.

As shown in detail below, knowing firstly the thickness of the bone tissue through which the given X-ray has passed and secondly the level of the attenuation of this X-ray that can be attributed solely to passing through the bone tissue, it is possible to calculate a bone mineral density referred to as an "areal" density that corresponds to the bone tissues through which the given X-ray has passed. Knowing the attenuation coefficients of the bone tissues as estimated with the various rays passing through the bone structure of interest, characterizing the projected image of that structure, it is possible to calculate the areal bone mineral density.

It should be observed that in addition to the above method of determining the attenuation coefficient associated with soft tissues only, it is also possible to use a method that involves a calibration testpiece presenting a plurality of zones, each having a known corresponding attenuation coefficient.

This method consists in placing one or more testpieces, each presenting at least one known attenuation coefficient beside the person while projecting X-rays from the sources to the detection surfaces.

Thereafter, by studying the gray scale or color or contrast levels in the first and second X-ray images, it is possible to obtain a correspondence between each known attenuation coefficient of a testpiece and a corresponding gray or color or contrast level in the image.

It is thus simple to estimate the attenuation suffered by each given X-ray projected onto a given detection surface by searching in a projection zone of the testpiece that is visible in one of the first and second X-ray images for an associated gray, color, or contrast level that is equivalent to the observed gray, color, or contrast level at a point of the image corresponding to the point of contact between the given X-ray and the corresponding detection surface. It is thus possible to determine the intensity attenuation suffered by each given X-ray after passing through the tissues of the person.

Specifically, two points of the image that present similar intensities have the same values for the product $\mu \times$thickness, where $\mu$ is the attenuation coefficient specific to the material passed through by an X-ray, and where the thickness is the thickness of that material through which the X-ray passes. Thus, knowing the thickness of the medium that has been passed through and the thickness of the testpiece, it is possible to estimate $\mu$ for the soft tissues that have been passed through.

By correction, it is then possible to estimate the mean coefficient of the hard tissue that has been passed through.

In a preferred implementation, in order to obtain the two images with different first and second angles of incidence, it is possible to cause the second X-ray image of said at least one portion of skeleton to be generated by observing a projection of X-rays coming from a second source that is distinct and spaced apart from the first source onto a second detection surface that is likewise distinct and spaced apart from the first detection surface.

In a particular implementation of the invention, said geometrical representation in three dimensions of said at least one portion of the outline containing said portion of the person's skeleton is deduced using at least one observation of the outline made using optical capture means.

Ideally, the geometrical representation in three dimensions of the outline of the person and the first and second radiological images are respectively positioned in a common three-dimensional reference frame and they preferably correspond to a single instant of observing the person, thus making it possible to facilitate the calculations needed for measuring the distribution of bone mineral density in the observed portion of the skeleton.

Finally, it should be observed that in certain circumstances it is possible to generate a geometrical representation in three dimensions of the outline of the person by using the first and second X-ray images.

For this purpose, the software identifies in the first and second X-ray images parameters that are characteristic of the person such as the relative three-dimensional positions between points characteristic of the skeleton and/or of the outline of the person and that are visible in these first and second images, or dimensions and distances between characteristic points of the skeleton and/or of the outline visible in the first and second images.

Thereafter, the software generates a geometrical representation in three dimensions of the person's outline using the characteristic parameters of the person as identified and using a statistical database previously prepared for a population of people, this database illustrating relationships between characteristic parameters of people and the expected representations in three dimensions of the outline of a person.

BRIEF DESCRIPTION OF THE DRAWING

Other characteristics and advantages of the invention appear clearly from the following description given by way of non-limiting indication and with reference to the accompanying drawings, in which.

DETAILED DESCRIPTION OF THE INVENTION

Figure 1:
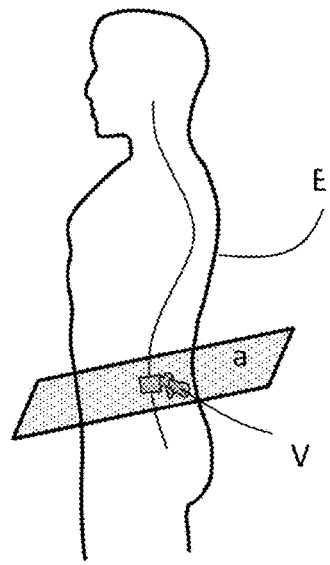
FIG. 1 is a lateral view of a person, in which view there can be seen the outline E of the person and an observation plane "A" selected for observing a portion of the person's skeleton and outline, in this example in cross-section.

As mentioned above, the invention relates to a method of estimating the distribution of bone mineral density in at least a portion V of a person's skeleton.

The invention also relates to a device for implementing the method. As can be seen in FIGS. 1a and 2, the device may comprise first and second detection surfaces P1 and P2 that are respectively plane and oriented relative to each other at an angle of 90°, with an angle uncertainty of plus or minus 60° and preferably of plus or minus 5° of angle and more preferably less than 1° of angle, as shown in FIGS. 1a and 2.

The device also comprises:

- a first X-ray source X, referred to as the posterioanterior source Spa for projecting X-rays towards and onto the first detection surface P1 after passing through the person going from the person's posterior face towards the anterior face; and
- a second X-ray source X, referred to as the lateral source Slat for projecting X-rays towards and onto the second detection surface P2 by passing through the lateral faces of the person.

The device also has a computer and software for performing calculations or estimations or deductions needed for implementing the method of the invention, the device thus being automatic or at least semi-automatic so as to enable the areal or volume distribution of bone mineral density (BMD) to be estimated in at least a portion of a person's skeleton.

It should be observed that the device may be constituted by a movable source and calibration means for determining in each of the views the overall radiological environment (position of the sources relative to the films and relative positions of the sources), and where necessary markings on the subject enabling a subject to be positioned in an overall environment.

The device may also be constituted by a single source and a rotation and calibration device enabling the subject to be turned and to define the pair of images while taking account of the turning of the subject in order to have the two different angles of incidence.

The device of the invention may also include optical capture means for observing the outline E of the person. These optical capture means, which are connected to the computer, serve to generate a three-dimensional geometrical representation of at least a portion of the outline E containing said portion of the person's skeleton.

These optical capture means (not shown) may comprise a body scanner or an optionally stereoscopic camera.

These optical capture means may optionally be associated with means for projecting moire fringes or a texture screen, optionally generated by projecting lights onto the person's outline. By way of example, these projection means may be adapted to project the fringes or the screens in the form of laser light.

In order to facilitate analysis of the images obtained by the device of the invention, the positions of the first and second detection surfaces and the positions of the first and second X-ray sources, and possibly also the positions of the optical capture means are located in a common space by using a three-dimensional reference frame.

The purpose of the method of the invention is to be able to provide an estimate of the bone mineral density (BMD) distribution in a portion of a person's skeleton.

The portion of the skeleton that is more particularly targeted for estimating BMD distribution is essentially a vertebral body or a vertebra, or else the neck of a femur or more generally a femur. These portions are targeted since they are particularly appropriate for characterizing the risk of osteoporosis or a change in mineral density.

Initially, in order to implement the method of the invention, the following are generated:

- a three-dimensional geometrical representation of said portion V of the person's skeleton for which it is desired to study BMD distribution; and
- a three-dimensional geometrical representation of at least a portion of the outline E containing said portion V of the person's skeleton; and
- at least one first X-ray image of said at least one portion of the skeleton, this first image being generated by observing a projection onto the first detection structure P1 of X-rays coming from the first source Spa; and
- at least one second X-ray image of said at least one portion of the skeleton, the second image being generated by observing a projection onto a second detection surface of X-rays coming from a second source Slat that is distinct and spaced apart from the first source.

Ideally, these first and second images correspond respectively to a single instant of detecting X-rays projected onto the first and second detection surfaces. The term "single" instant is used to mean that the time difference between the detections needed for generating the first and second images is less than 1 second, and preferably less than 0.5 seconds.

Ideally, since the purpose is to obtain a BMD distribution on the skeleton, e.g. for the purpose of analyzing a risk of osteoporosis, the first and second images are taken to show projections of the person in a standing position. The standing position of a person is more representative of the risk associated with osteoporosis.

Although it is possible to obtain said geometrical representation in three dimensions of said at least one portion of the outline containing said portion of the person's skeleton from an observation of the person taken using the optical capture means, it is also possible for this geometrical representation in three dimensions to be deduced from said first and second X-ray images.

In certain circumstances, it is possible to combine both techniques, with the optical capture means serving to ensure accuracy for the representation of the outline, and the use of the first and second images serving to ensure that the representation of the outline is well positioned in the same three-dimensional reference frame as the representation in three dimensions of the portion of the skeleton that is to be viewed.

When the optical capture means provide only one view of the outline, and assuming that a 3D model of a vertebra is estimated from the X-ray image only, it is possible to estimate the thicknesses of soft tissue that has been passed through and to evaluate the attenuation of the X-rays due to those soft tissues. The areal BMD of the vertebra can thus be estimated, but with reduced accuracy.

It should be observed that several solutions exist for determining a geometrical representation in three dimensions of said portion of the person's skeleton.

Reference may be made for example to the solutions shown in patents FR 2 856 170 and WO 2008/146069.

The publication by L. Humbert, J. A. De Guise, B. Aubert, B. Godbout, and W. Skalli: "3D reconstruction of the spine from biplanar X-rays using parametric models based on transversal and longitudinal inferences", Med. Eng. Phys. 2009, July; 31(6): pp. 681-7 describes an example of methodology for reconstructing a virtual model of a portion of a person's skeleton using biplanar X-rays, by generating images of the same type as said first and second X-ray images.

The following two publications deal with 3D reconstruction both of the skeleton and of the outline.

The publication "Personalized body segment parameters from bipolar low-dose radiography" by Raphael Dumas, Rachid Aissaoui, Member, IEEE, David Mitton, Wafa Skalli, and Jacques A. de Guise, published in the journal IEEE Transactions on Biomedical Engineering, Vol. 52, No. 10, October 2005, also describes a methodology for reconstructing a virtual model of a portion of a person's skeleton using biplanar X-rays, by generating images of the same type as said first and second X-ray images. That methodology is incorporated herein by reference since it gives an example of obtaining a virtual model representative of a portion of the skeleton and/or a geometrical representation in three dimensions of said portion of the person's skeleton. That type of model obtained in compliance with the method described in that publication can be used for implementing the present invention.

Likewise, the publication "Subject-specific body segment parameters estimation using biplanar X-rays: a feasibility study" by Baptiste Sandoz, Sébastien Laporte, Wafa Skalli, and David Mitton CNRS, Arts et Métiers Paris Tech., LBM, 151 bd. de l'Hôpital, 75013 Paris, France, published in the journal "Computer Methods in Biomechanics and Biomedical Engineering", Vol. 13, No. 6, December 2010, pp. 649-654, by the publisher Taylor & Francis, also describes a method making it possible, from X-ray images of the same type as said first and second images generated in distinct non-parallel planes, to obtain a virtual model representative of a portion of the skeleton and of the outline.

That type of model obtained in compliance with the method described in that latter publication can be used for implementing the present invention.

After determining:
  the geometrical representation in three dimensions of said portion of the person's skeleton; and
  the geometrical representation in three dimensions of the outline E;
  the software acts automatically for each given X-ray Rx to estimate:
    values for the thicknesses L1, L2 of soft tissues through which this given X-ray Rx has passed;
    a value for thickness L0 of the bone tissue through which this given X-ray Rx has passed; and
    a value of the overall attenuation of the given X-ray, between its source and its projection onto the detection surface where it is projected.

The value for the attenuation of a given X-ray for tissue of thickness x is calculated from the intensity $I_0$ of the X-ray (also referred to as the incident beam) leaving the source Slat or Spa, and from the intensity I of the same X-ray leaving the tissue through which it has passed, by using the following formula:

$$I = I_0 e^{-\mu x}$$

where μ is the attenuation coefficient of the tissue.

The overall attenuation value for a given X-ray passing through a plurality of tissues of thickness $x_i$ and attenuation coefficients $\mu_i$ is calculated from the intensity $I_0$ of the X-ray (also referred to as the incident beam) leaving the source Slat or Spa, and from the intensity I of the same X-ray as detected at a unit point or pixel of the corresponding image, using the following formula:

$$I = I_0 e^{-\Sigma \mu_i x_i}$$

The software executed by the computer uses the value for the thicknesses of the soft tissues through which the given X-ray has passed to calculate:
  firstly a value for the attenuation of the given X-ray by the thickness of soft tissues to which it has passed; and
  secondly a value for the attenuation of the given X-ray by the thickness of the bone tissue through which it has passed.

Using the value for the thickness of bone tissue through which the given X-ray has passed, the value for the attenuation of the given X-ray by the thickness of soft tissues only through which it has passed, and the value for the overall attenuation of the given X-ray, the software estimates a value that is representative of the bone mineral density of the bone tissue V through which the given X-ray has passed.

Figure 1A:
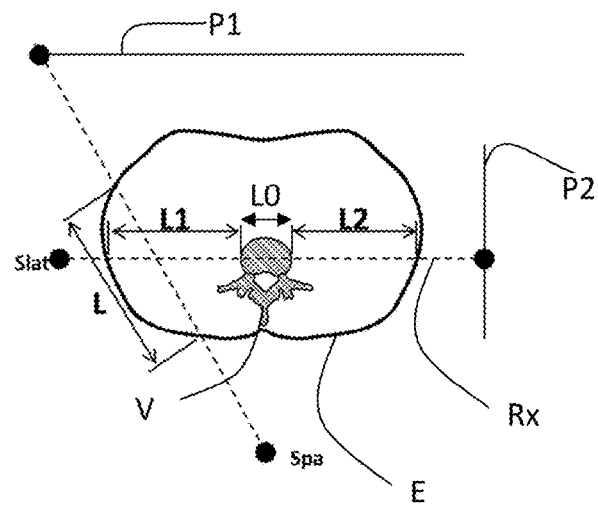
FIG. 1a is a cross-section view of the portion of the person's skeleton on the observation plane "A" when the person's soft tissues are considered as being relatively uniform from the point of view of their attenuation coefficients, and in this figure there can be seen first and second sources Slat and Spa for projecting X-rays and first and second plane surfaces P1 and P2 (detection planes) for detecting X-rays, each detection surface presenting a plurality of detection points, each adapted to detect an intensity of X-rays projected onto the detection point.
Figure 2:
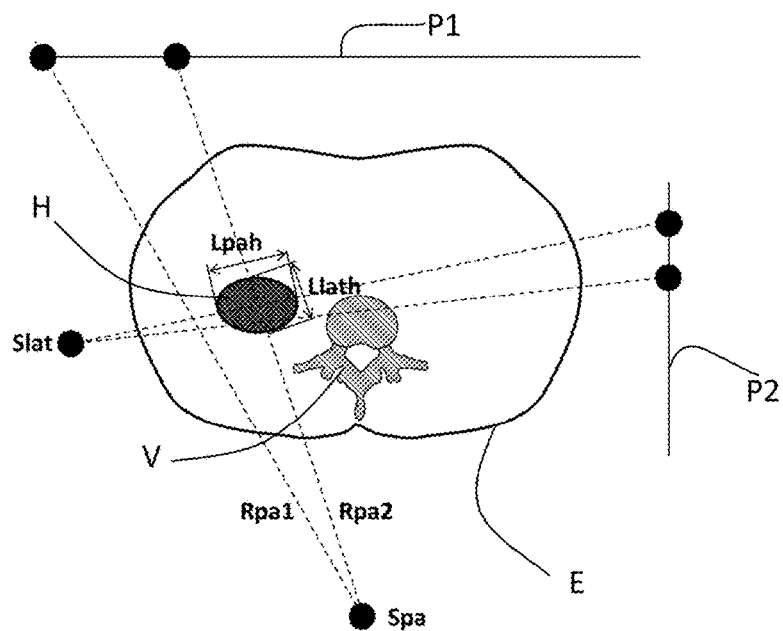
FIG. 2 shows the same view as FIG. 1a, but in this example the person presents a non-uniformity H of soft tissues leading to a plurality of attenuation coefficients being taken into account, specifically a coefficient that needs to be determined for each soft tissue non-uniformity in order to be able to estimate the bone mineral density distribution while limiting the noise generated by the soft tissues surrounding the bones and by the non-uniformities of those soft tissues.

With reference to FIGS. 1, 1*a*, and 2, there follows an explanation of an example of estimating BMD distribution for a vertebra V.

In FIG. 1*a*, the soft tissues, i.e. organs other than the hard tissues of the skeleton, have an X-ray attenuation coefficient that is substantially uniform.

In contrast, in the example of FIG. 2, the soft tissues include a non-uniformity that presents an attenuation coefficient that is different from the attenuation coefficient of the other soft tissues. This example serves to explain how the device of the invention, which includes a computer and the above-described software, implements the method of the invention in automatic manner.

Note Concerning the X-Ray Attenuation Equation

Let $I_0$ be the intensity of the incident beam emitted by the source, I be the intensity of the beam/ray as detected on a pixel of the image, p the attenuation coefficient of the material through which the beam passes, and x the thickness passed through in that material.

$$I = I_0 e^{-\mu x} \quad (1)$$

If there are a plurality of media $\mu_i$ having a plurality of different thickness $x_i$, then the attenuation equation becomes:

$$\frac{I}{I_0} = e^{-\Sigma \mu_i x_i} \quad (2)$$

An example of using formulas 1 and 2 for estimating the bone mineral density of a vertebra (FIG. 1):

Let there be a given vertebra V together with two biplanar sources suitable for giving posterioanterior and lateral X-ray attenuations PA and Lat, and an incident ray passing through the vertebra in the lateral view Lat, under the following circumstance:

L1 and L2 are the thicknesses of soft tissues passed through on either side of the vertebra V:
  $\mu_m$ is the attenuation coefficient of the soft tissues (which coefficient may itself be subdivided into a plurality of coefficients, e.g. $\mu_{m1}$ and $\mu_{m2}$); and
  $\mu_{vi}$ the various attenuation coefficients of the vertebra (non-uniform medium) along the line defining the path followed by the incident ray through the vertebra, with $x_{vi}$ being the thicknesses passed through along that line.

This gives:

$$\frac{I}{I_0} = e^{-\mu_m L_1 - \mu_m L_2 - \Sigma \mu_{vi} x_{vi}} \quad (3)$$

and thus $$\frac{I}{I_0} = e^{-\mu_m (L_1 + L_2) - \Sigma \mu_{vi} x_{vi}} \quad (4)$$

and thus $$\frac{I}{I_0 e^{-\mu_m (L_1 + L_2)}} = e^{-\Sigma \mu_{vi} x_{vi}} \quad (5)$$

It is thus possible to reconstruct the "areal BMD" image that includes the bone signal, and that is obtained for each incident ray (and thus each pixel) by taking into consideration the corrected I term ($I_{corr}$):

$$I_{corr} = \frac{I}{I_0 e^{-\mu_m(L_1+L_2)}}$$

With this modification of the signal, it is possible to consider the technique known in single-energy X-ray absorptiometry (SXA), as described for example in the publication by G. Mabilleau et al. for an isolated bone (G. Mabilleau, A. Mieczkowska, H. Libouban, Y. Simon, M. Audran, D. Chappard, "Comparison between quantitative X-ray imaging, dual energy X-ray absorptiometry, and microCT in the assessment of bone mineral density in disuse-induced bone loss", J. Musculoskelet. Neuronal. Intearct. 2015 March; 15(1): pp. 42-52).

A calibration may be undertaken using a calibration phantom (testpiece), generally made of Lucite (having a coefficient of attenuation that is close to that of soft tissues) and of aluminum (having a coefficient of attenuation that is close to that of bone), and then the signal is redistributed over this range of values in order to highlight the bone signal, making it possible to end up with the areal BMD, and to do so with a single-energy image.

Remarks:

1) Calibration: for calibration (FIG. 1a or 2), advantage can be taken of the fact that there are zones that are constituted by soft tissues only and for which the length L of the thickness passed through is known, thus making it possible to obtain directly the attenuation coefficient of the soft tissues of the subject in question.

2) Highlighting "bone" contrast: this "bone" image, makes it possible during calibration to eliminate the soft tissue signal and to redistribute the signal over the range from soft tissue to bone, thereby highlighting the contrast, and thus producing a signal that can be useful for 3D reconstruction.

3) Presence of non-uniformities: because of variations between different people and because of specific features applying to the moment X-rays are taken, it is possible to have local non-uniformities in the attenuation coefficient, thereby disturbing the signal. If calibrated biplanar X-rays are available (FIG. 2), it is possible on the X-rays (posterioanterior and lateral) for example to estimate the size of the non-uniform element (given the index h), and to correct its effect as follows:

1/ estimate Lpah and Llath (from the calibrated biplanar X-rays and from a geometrical model for the non-uniformity);

2/ in the posterioanterior view, for the rays Rpa1 that pass through the soft tissues without non-uniformity, and knowing the thicknesses passed through, it is possible to deduce $\mu_m$ (soft tissue attenuation coefficient);

3/ for a ray Rpa2 that passes through the non-uniformity over a total length Lpa2 including Llath in the medium h, the signal in the image results from $\mu_m$ ($L_{pa}-L_{lath}$ and $\mu_h L_{lath}$), which makes it possible to deduce $\mu_h$;

4/ in order to produce the BMD image in lateral view, the overall thicknesses passed through "outside bone" is known (L1+L2), the thickness passed through in the non-uniformity $L_{pah}$ is also known (from the PA view), as are the attenuation coefficients $\mu_m$ and $\mu_h$, thus making it possible to use equation 2 and the reasoning deployed for equations 3 to 6 to obtain the BMD image as defined by the following term:

$$I_{corr} = \frac{I}{I_0 e^{-\mu_m(L_1+L_2-L_{pah})-\mu_h(L_{pah})}}$$

The value of $I_{corr}$ makes it possible to obtain a value known as the "areal BMD", as is generally obtained using reference imaging modalities (DXA corresponding to the method of imaging by dual X-ray absorptiometry), this areal BMD value does not take account of the non-uniformity of the vertebral tissue that has been passed through.

It is also possible, using this areal BMD image, to estimate a volume density distribution using the method described by Travert (science thesis available at https://tel.archives-ouvertes.fr/file/index/docid/834740/filename/TRAVERT.pdf, entitled "Estimation du risque de fracture ostéoporotique du rachis thoraco-lombaire par un modele en élément finis personnalisé" [Estimating the risk of osteroporesis fracture of the thoracic lumbar spine by a personalized finite element model] defended at ENSAM in 2012: briefly it involves positioning a vertebra having a generic distribution of bone mineral density, and adjusting that distribution from the areal BMD given in one of the views, or iteratively from areal BMD data obtained from both views).

It is thus possible, using the software/program executed by a computer and analyzing the first and second images generated by projecting X-rays, to estimate the positions where rays cross in three dimensions, each crossing position characterizing a crossing between a given ray coming from the first source and another given ray coming from the second source. It is possible to associate volume bone mineral density values with at least some of the crossing points.

The invention claimed is:

1. An estimation method for estimating the bone mineral density distribution in at least one portion of a person's skeleton, the skeleton being made up of bone tissue, the bone tissue being surrounded by soft tissue, in turn surrounded by an outline (E) of the person, the method being characterized in that it comprises generating:

a geometrical representation in three dimensions of said portion of the person's skeleton;

a geometrical representation in three dimensions of at least one portion of the outline (E) containing said portion of the person's skeleton;

at least one first X-ray image of said at least one portion of the skeleton, this first image being generated by observing a projection onto a first detection surface of X-rays, coming from a first source, the first image being generated by projecting X-rays and representing the person as observed from a first observation angle of incidence; and at least one second X-ray image of said at least one portion of the skeleton, the second image being generated by projecting X-rays and representing the person as observed from a second observation angle of incidence distinct from the first observation angle of incidence; and then using predetermined software and for a plurality of given X-rays selected from among said projected X-rays, estimating for each given X-ray:

a value for the thickness of soft tissue through which the given X-ray has passed;

a value for the thickness of bone tissue through which the given X-ray has passed; and a value for the overall attenuation of the given X-ray between its source and its projection onto the detection surface onto which it is projected; and using the thickness value for soft tissue through which the given X-ray passes, and using an estimate for an attenuation coefficient of the soft tissues through which the given X-ray passes, deducing firstly a value for the attenuation of the given X-ray due to the thickness of soft tissue through it has passed and secondly a value for the attenuation of the given X-ray due to the thickness of bone tissue through which it has passed; and then using the value for the thickness of bone tissue through which the given X-ray has passed, the value for the attenuation of the given X-ray due to the thickness of bone tissue through which it has passed, and the overall value for attenuation of the given X-ray, the software estimates a value representative of the bone mineral density of the bone tissue through which the given X-ray has passed.

2. The estimation method according to claim 1, wherein said second X-ray image of said at least one portion of the skeleton is generated by observing a projection onto a second detection surface of X-rays coming from a second source that is distinct and spaced apart from the first source.

3. The estimation method according to claim 2, wherein the first and second detection surfaces are respectively plane and oriented relative to each other at an angle of 90° plus or minus 60°, and preferably plus or minus 5° of angle.

4. The estimation method according to claim 1, wherein in order to deduce said value for the attenuation of said given X-ray due to the thickness of soft tissue through which it has passed, the software estimates an attenuation coefficient for the soft tissues of the person.

5. The estimation method according to claim 4, wherein in order to estimate the attenuation coefficients of the soft tissues of the person, the software looks for a particular X-ray that passes solely through soft tissues of the person without passing through bone tissues, and from the position of this particular X-ray and from the geometrical representation in three dimensions of the portion of the outline (E), the software estimates the value of the thickness of soft tissues through which this particular X-ray passes, and by observing a projection point of this particular X-ray, the software determines a value for the attenuation to which the particular X-ray is subjected on passing solely through soft tissues of the person, and then knowing said thickness value for the soft tissues through which a particular X-ray passes and said value for the attenuation to which the particular X-ray is subjected, the software calculates the attenuation coefficient associated solely with the person's soft tissues.

6. The estimation method according to claim 5, wherein, knowing:

the attenuation coefficient of the person's soft tissue;

the thickness of the soft tissue through which the given X-ray passes;

the intensity ($I_0$) of the given ray at its source; and the intensity (I) of the given ray as detected on the detection surface (P1, P2) onto which it is projected;

the software calculates:

firstly a value for the attenuation of the given X-ray due to the thickness of the soft tissue through which it has passed; and secondly, a value for the overall attenuation of the given X-ray, between its source and the detection surface onto which it is projected; and then by correcting this overall attenuation value of the given X-ray by using said attenuation value of the given X-ray due to the thickness of soft tissue through which it has passed, the software calculates the value of the attenuation of the given X-ray due to the thickness of bone tissue through which it has passed.

7. The method according to claim 1, wherein said value representative of the bone mineral density of bone tissue through which the given X-ray passes is an attenuation coefficient of the bone tissue through which the given X-ray passes.

8. The method according to claim 1, wherein said first and second images correspond respectively to detecting X-rays projected onto the first and second detection surfaces at a common instant.

9. The method according to claim 1, wherein said first and second images correspond respectively to detecting X-rays projected onto said first and second detection surfaces at two distinct instants.

10. The method according to claim 1, wherein the first and second images illustrate projections of the person in the standing position.

11. The method according to claim 1, wherein said geometrical representation in three dimensions of said at least one portion of the outline containing said portion of the person's skeleton is deduced from said first and second X-ray images.

12. The method according to claim 1, wherein said geometrical representation in three dimensions of said at least one portion of the outline containing said portion of the person's skeleton is deduced using an observation of the outline made using optical capture means.

13. A device for implementing the method according to claim 1.

* * * * *